US011529445B2

(12) United States Patent
Tumlin (10) Patent No.: US 11,529,445 B2
(45) Date of Patent: *Dec. 20, 2022

(54) METHODS AND APPARATUS FOR KIDNEY DIALYSIS AND EXTRACORPOREAL DETOXIFICATION

(71) Applicant: HIBAR Microsciences LLC, Atlanta, GA (US)

(72) Inventor: James A. Tumlin, Buford, GA (US)

(73) Assignee: HIBAR Microsciences LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/026,251

(22) Filed: Sep. 20, 2020

(65) Prior Publication Data

US 2021/0069400 A1    Mar. 11, 2021

Related U.S. Application Data

(63) Continuation of application No. 15/978,611, filed on May 14, 2018, now abandoned, which is a
(Continued)

(51) Int. Cl.
*A61M 1/16* (2006.01)
*A61M 1/34* (2006.01)
(Continued)

(52) U.S. Cl.
CPC ............ *A61M 1/1676* (2014.02); *A61M 1/16* (2013.01); *A61M 1/3496* (2013.01);
(Continued)

(58) Field of Classification Search
CPC .... A61M 1/1676; A61M 1/16; A61M 1/3496; A61M 1/3643; A61M 1/3644;
(Continued)

(56) References Cited

U.S. PATENT DOCUMENTS

| 4,919,811 A | 4/1990 | Davis |
| 5,744,042 A | 4/1998 | Stange et al. |

(Continued)

FOREIGN PATENT DOCUMENTS

| CN | 101838239 A | 9/2010 |
| JP | H10-108907 A | 4/1998 |

(Continued)

OTHER PUBLICATIONS

Romana Stopkova et al, Multiple roles of secretory lipocalins (Mup, Obp) in mice, Folia Zool., vol. 58, Supplement 1, pp. 29-40, published 2009. (Year: 2009).*

(Continued)

*Primary Examiner* — Joseph W Drodge
(74) *Attorney, Agent, or Firm* — HDC IP Law, LLP; Sam L. Nguyen (57) ABSTRACT

The present disclosure relates to a dialysis apparatus comprising a membrane having at least one protein from the lipocalin family bound thereon. The disclosure further relates to methods of removing non-polar, hydrophobic and/or protein bound uremic toxins from a target subject utilizing the dialysis apparatus described herein as well as methods of extracorporeal detoxification.

8 Claims, 4 Drawing Sheets

Related U.S. Application Data continuation of application No. 14/738,308, filed on Jun. 12, 2015, now Pat. No. 9,968,722, which is a continuation-in-part of application No. PCT/US2014/071212, filed on Dec. 18, 2014.

(60) Provisional application No. 62/031,257, filed on Jul. 31, 2014, provisional application No. 61/919,024, filed on Dec. 20, 2013.

(51) Int. Cl.
  *A61M 1/36* (2006.01)
  *B01D 61/24* (2006.01)
  *B01D 71/16* (2006.01)
  *B01D 71/56* (2006.01)
  *B01D 71/68* (2006.01)
  *B01J 20/24* (2006.01)
  *B01D 71/42* (2006.01)

(52) U.S. Cl.
  CPC ........ *A61M 1/3643* (2013.01); *A61M 1/3644* (2014.02); *A61M 1/3649* (2014.02); *A61M 1/3679* (2013.01); *B01D 61/243* (2013.01); *B01D 71/16* (2013.01); *B01D 71/42* (2013.01); *B01D 71/56* (2013.01); *B01D 71/68* (2013.01); *B01J 20/24* (2013.01); *B01D 2311/2626* (2013.01); *B01D 2311/2688* (2013.01); *B01J 2220/4856* (2013.01)

(58) Field of Classification Search
  CPC .... A61M 1/3649; A61M 1/3679; A61M 1/36; A61M 1/362; A61M 1/3621; A61M 1/3633; A61M 1/34; B01D 71/16; B01D 71/42; B01D 71/56; B01D 71/68; B01D 2311/2626; B01D 2311/2688; B01D 61/24; B01D 61/243; B01D 61/30; B01D 2252/20; B01D 2252/205; B01D 2253/20; B01J 2220/4856; B01J 20/22; B01J 20/24; B01J 20/28033; A61P 39/06
  See application file for complete search history.

(56) References Cited

U.S. PATENT DOCUMENTS

| | | | |
|---|---|---|---|
| 5,972,905 A | 10/1999 | Hosokawa et al. | |
| 9,968,722 B2 * | 5/2018 | Tumlin | A61P 39/06 |
| 2002/0146814 A1 | 10/2002 | Nilsson | |
| 2003/0224444 A1 | 12/2003 | Sabbadini et al. | |
| 2004/0147437 A1 | 7/2004 | Findlay | |
| 2008/0254035 A1 * | 10/2008 | Yorke-Smith | A61P 27/02 424/139.1 |
| 2008/0286269 A1 | 11/2008 | Violette et al. | |
| 2009/0092582 A1 * | 4/2009 | Bogin | A61P 5/00 424/85.5 |
| 2009/0305963 A1 | 12/2009 | Sukhatme et al. | |
| 2010/0135976 A1 | 6/2010 | Nilsson et al. | |
| 2011/0033469 A1 | 2/2011 | Godfroid et al. | |
| 2011/0237513 A1 | 9/2011 | Kas | |
| 2011/0262353 A1 | 10/2011 | Skerra et al. | |
| 2012/0111795 A1 | 5/2012 | Chamuleau et al. | |
| 2012/0190096 A1 | 7/2012 | Siekmann et al. | |
| 2012/0323224 A1 | 12/2012 | Humes et al. | |
| 2013/0011900 A1 | 1/2013 | Siekmann et al. | |
| 2013/0098834 A1 | 4/2013 | Axelsson | |
| 2013/0217637 A1 | 8/2013 | Barasch et al. | |
| 2014/0038203 A1 | 2/2014 | Arthur et al. | |
| 2014/0141986 A1 | 5/2014 | Spetzler et al. | |
| 2014/0175018 A1 | 6/2014 | Winqvist et al. | |
| 2014/0288008 A1 * | 9/2014 | Matschiner | A61K 38/1709 435/7.4 |

FOREIGN PATENT DOCUMENTS

| | | | |
|---|---|---|---|
| WO | 97/32893 A1 | 9/1997 | |
| WO | 97/48483 A1 | 12/1997 | |
| WO | 2005/059564 A1 | 6/2005 | |
| WO | 2006/091035 A1 | 8/2006 | |
| WO | 2008/155134 A1 | 12/2008 | |
| WO | 2010/006809 A2 | 1/2010 | |
| WO | 2010/045474 A1 | 4/2010 | |
| WO | 2010/006809 A3 | 5/2010 | |
| WO | 2012/163544 A1 | 12/2012 | |
| WO | 2013/138338 A2 | 9/2013 | |
| WO | 2013/138338 A3 | 12/2013 | |
| WO | 2015/095553 A1 | 6/2015 | |

OTHER PUBLICATIONS

C. Nespoulous et al, "Odorant Binding and Conformational Changes of a Rat Odorant-binding Protein", Chem. Senses, vol. 29, pp. 189-198, published 2004. (Year: 2004).*
Karthikeyan et al., "Identification of p-Cresol as an Estrus-specific Volatile in Buffalo Saliva: Comparative Docking Analysis of Buffalo OBP and β-lactoglobulin with p-Cresol", Zoological Science, vol. 31(1), pp. 31-36 (2014).
Schlehuber et al., "Lipocalins in drug discovery: from natural ligand-binding proteins to 'anticalins'", Drug Discovery Today, vol. 10(1), pp. 23-33 (2005).
Whitson et al., "Human Odorant Binding Protein 2a has Two Affinity States and is Capable of Binding Some Uremic Toxins", Biochemistry & Analytical Biochemistry, vol. 3(2), article 1000156 (2014).
WIPO, ISR for PCT/US2014/071212, mailed Mar. 10, 2015, published Jun. 25, 2015.
WIPO, WO-ISA for PCT/US2014/071212, mailed Mar. 10, 2015, published Jun. 25, 2015.
WIPO, Transmittal for IPRP for PCT/US2014/071212, mailed Jun. 30, 2016.
EPO, Partial SESR for EP14872502.1, Aug. 4, 2017.
EPO, EESR for EP15171983.8, Apr. 13, 2016.
EPO, Result of consultation for EP15171983.8, May 29, 2019.

* cited by examiner

METHODS AND APPARATUS FOR KIDNEY DIALYSIS AND EXTRACORPOREAL DETOXIFICATION

STATEMENT OF PRIORITY

This application is a continuation of U.S. application Ser. No. 15/978,611, filed May 14, 2018, now abandoned; which is a continuation of U.S. application Ser. No. 14/738,308, filed Jun. 12, 2015, now U.S. Pat. No. 9,968,722, which claims the benefit, under 35 U.S.C. § 119(e), of U.S. Provisional Application Ser. No. 61/919,024, filed Dec. 20, 2013 and 62/031,257, filed Jul. 31, 2014, and is a continuation-in-part of International Application No. PCT/US2014/071212, filed Dec. 18, 2014. The entire contents of each of which are hereby incorporated herein by reference in their entireties.

TECHNICAL FIELD

The present disclosure relates to a method and dialysis apparatus designed to facilitate the clearance of hydrophobic, protein bound uremic toxins from subjects with impaired kidney function and/or affected by drug overdose.

BACKGROUND

Hemodialysis, hereinafter referred to as kidney dialysis, or simply "dialysis," is a medical procedure that is performed on target subjects, for example humans, (and also, on a smaller scale, pet animals), to remove accumulated waste and toxins from the blood in a similar manner to a functioning kidney. When a person or animal's kidneys cease to function properly due to one or more of a number of acute or chronic diseases or conditions (e.g., diabetes, glomerulonephritis and hypertension are commonly recognized medical conditions that are associated with the development of renal failure), toxins accumulate in the bloodstream.

Failure to remove such accumulated waste and toxic compounds—primarily urea, uric acid and its analogues, and other nitrogenous compounds such as creatinine; and excess amounts of elements such as potassium, phosphorous, sodium, chloride and other minerals from the blood results in deterioration of body tissues and organ systems, which eventually results in death if untreated. Moreover, failure to remove such waste and toxins may result in uremia, which is a clinical syndrome that in many aspects resembles systemic poisoning. Almost every organ system in the body is affected by uremic toxicity and the known uremic clinical symptoms and side effects include, but are not limited to, fatigue, anemia, itching, peripheral neuropathy, gastrointestinal disorders including nausea, vomiting, diarrhea, cardiovascular complications including accelerated coronary and peripheral vascular disease, left ventricular hypertrophy, cardiac fibrosis and accelerated rates of arrhythmias. Conventional hemodialysis is capable of treating uremic symptoms that arise from "water soluble" non-hydrophobic uremic toxins, but dialysis is very ineffective in treating symptoms that arise from hydrophobic, protein-bound uremic toxins.

Generally, dialysis interposes a semi-permeable membrane between a flowing stream of blood and an appropriate rinsing solution. By convective and diffusive transport, the composition of body fluids approaches that of the dialysis solution. Dialysis may be performed in a hospital setting or clinic; or in some cases, the target subject is trained to perform the procedure at home on an outpatient basis. Two primary types of dialysis are regularly performed—conventional hemodialysis and peritoneal dialysis. In conventional hemodialysis, the target subject is connected (via an arteriovenous fistula, graft or by catheter) to a dialysis machine. The dialysis machine functions to pump the contaminated blood from the target subject through a dialyzer, where the blood is filtered through a dialyzing solution, thereby lowering the concentration of accumulated waste (e.g., urea), and thence returned to the target subject. Current dialysis membranes and technology are capable of clearing water soluble uremic toxins, but exhibit limited clearance of non-polar, hydrophobic, or protein bound toxins.

For example, cresol is an organic compound with the formula $CH_3C_6H_4(OH)$. It is a colourless solid that is a derivative of phenol and an isomer of o-cresol and m-cresol. A limitation of current dialysis treatment is the inability to remove all toxins from the bloodstream during a dialysis procedure. In particular, small hydrophobic compounds such as p-cresol, are known to build up and have the potential to cause severe toxicity. Current dialysis membranes and technologies are able to clear water soluble uremic toxins, but have limited clearance of non-polar protein bound toxins. Non-polar uremic toxins include, but are not limited to, p-cresol, p-cresol sulfate, and indoxyl sulfate. Thus, many target subjects, including patients undergoing kidney dialysis procedures, especially target subjects with advanced kidney disease have an accumulation of p-cresol in the plasma.

Further; p-cresol is derived from phenylalanine metabolism and has one of the highest plasma level of any known non-polar uremic toxins. Moreover, p-cresol, indoxyl sulfate and other protein bound uremic toxins have been linked to the development of vasculopathy, left ventricular hypertrophy, cardiac fibrosis as well as atrial and ventricular arrhythmias.

Accordingly, what is needed is a method and/or an apparatus that may be used during a dialysis procedure to remove hydrophobic, non-polar uremic toxins, such as p-cresol, from the blood.

BRIEF SUMMARY

In particular embodiments, the disclosure relates to a dialysis apparatus that includes materials including, but not limited to, polysulfone and other materials that are used for filtering accumulated toxins of patients with impaired kidney function. The dialysis materials in the present apparatus may be bound to one or more proteins in various combinations from the lipocalin family of proteins.

In other embodiments, the disclosure relates to a modified dialysis cartridge having at least one member of the lipocalin family. The apparatus may include a member of the olfactory binding proteins (OBP) and any other member of the lipocalin family of proteins that are covalently bound to dialysis filtering materials. The therapeutic purpose of bound lipocalin proteins will be to facilitate the removal non-polar, hydrophobic, water soluble, water insoluble and/or protein bound blood toxins that accumulate in the plasma of patients with advanced renal disease.

In further embodiments, the disclosure provides methods of removing non-polar, hydrophobic and/or protein bound uremic toxins from a target subject comprising using a dialysis apparatus having materials including, but not limited to, polysulfone and other materials that are used for filtering accumulated toxins of patients with impaired kidney function. The dialysis materials may be bound to one or more proteins in various combinations from the lipocalin family of proteins. Methods of removing non-polar, hydrophobic and/or protein bound uremic toxins from a target subject comprising using a dialysis apparatus may further comprise using a priming solution that is passed through the cartridge prior to use. The solution includes one or more lipocalins that would attach to the dialysis cartridge membrane.

In some embodiments, the disclosure provides methods of preventing or treating uremia including uremic clinical symptoms and side effects.

In some embodiments, the disclosure provides methods and apparatus for facilitating clearance or removal of prescription and non-prescription drugs from a subject.

In some embodiments, the disclosure provides methods and apparatus for facilitating clearance or removal of prescription and non-prescription drugs from a subject resulting from an overdose.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION

Reference now will be made in detail to the embodiments of the present disclosure, one or more examples of which are set forth hereinbelow. Each example is provided by way of explanation of the apparatus and/or methods of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as found within the scope of the appended claims and their equivalents. Other objects, features and aspects of the present disclosure are disclosed in or are apparent from the following detailed description. It is to be understood by one of ordinary skill in the art that the present discussion is a description of exemplary embodiments only and is not intended as limiting the broader aspects of the present disclosure.

The present disclosure relates generally to a dialysis apparatus that includes at least one protein from the lipocalin family. In some embodiments, the dialysis apparatus is a dialysis cartridge that has been modified to have at least one protein from the lipocalin family covalently bound to a membrane located within the blood side of the cartridge. In some embodiments, the at least one protein from the lipocalin family is bound to a polysulfone membrane. Additionally, the disclosure relates to methods of removing non-polar toxins, hydrophobic toxins and/or protein bound toxins from the blood of a target subject by utilizing a dialysis apparatus that includes at least one protein from the lipocalin family.

In general, a dialysis cartridge is a device comprising plastic and other materials that is designed to rapidly process large volumes of blood (e.g. 500 mls/min) from patients with no kidney function through a chamber that is composed of modified polymers (polysulfone or polyacrylamide materials) that can function to filter the blood of excess electrolytes waters and toxins generated by cellular metabolism (e.g., uremic toxins). These polymers are generally manufactured in the form of hollow fibers or arranged in stacked sheets (e.g., plate dialyzers) in a manner that allow blood to be exposed under varying degrees of pressure to one side of the polymer material. Pores or openings within the polymer allow for excess electrolytes, water and uremic toxins to flow through "pores" within the polymers and into a complex electrolyte solution (e.g., dialysate) flowing on the other side of the polymer. This structure allowing movement of electrolytes, water and uremic toxins with the blood of across a semi-permeable polymer membrane and into a dialysate solution is generally understood in the art to encompass the definition of a dialysis cartridge. A dialysis apparatus can include the use of large gauge hollow needles that are used to access either a dialysis fistula or catheter where blood from these needles is pumped through a dialysis cartridge at high pressure. This dialysis apparatus (as shown in the figures) can pump in a direction opposite to the flow of blood through the cartridge. This blood dialysate interface can maximize the process of movement of uremic toxins through the filter into the dialysate and out of the body. Thus, the dialysis apparatus may accomplish the process of clearance of excess electrolytes, water and uremic toxins.

The target subject is connected to a hemodialysis machine and the target subject's blood is pumped through the machine. Blood is accessed in patients requiring treatment with the present inventive concept by a central dialysis catheter, dialysis arteriovenous fistula or dialysis arterial graft. Dialysis procedures separate elements in a solution by utilizing, diffusion across a semi-permeable membrane (diffusive solute transport) down a concentration gradient. Waste, toxins, and excess water are removed from the target subject's blood and the blood is infused back into the target subject. Each dialysis treatment typically last between 3-4 hours and three times per week.

The hemodialysis technologies can be designed and configured for on-site or at-home dialysis treatments. Furthermore, dialysis apparatus can be used in portable dialysis treatment devices such as, for example, wearable artificial kidneys in which a target subject may move freely during dialysis.

The present disclosure provides a dialysis apparatus for providing clearance of non-polar uremic toxins in a target subject that includes patient's home hemodialysis, nocturnal hemodialysis and the potential of "wearable" portable dialysis machines.

In some embodiments, the present disclosure is directed to a dialysis apparatus comprising a body having an inlet and an outlet and defining an interior, the interior including a layer comprising at least one polysulfone membrane having at least one protein from the lipocalin family bound thereto. In some embodiments, the dialysis apparatus is constructed and arranged so that a fluid, such as blood or plasma, entering the apparatus contacts the at least one lipocalin protein upon entering the apparatus and before exiting the device through the outlet. In some embodiments, the dialysis apparatus comprises a polysulfone membrane having a plurality of proteins from the lipocalin family bound thereto. Still in some embodiments, where the polysulfone membrane includes a plurality of proteins, the plurality of proteins may be the same protein selected from the lipocalin family, or the plurality of proteins may comprise a combination of different types of proteins selected from the lipocalin family. In particular embodiments, the membrane is covalently bound to the at least one protein from the lipocalin family. Further, the membrane is specifically bound to the at least one protein from the lipocalin family.

Generally, the family of lipocalin proteins refers to a family of proteins that transport small hydrophobic molecules. Non-limiting examples of lipocalin family proteins include, but are not limited to the following, fatty acid binding proteins, olfactory binding proteins, and retinol binding proteins. Each protein within the lipocalin family shares limited regions of sequence homology and a common tertiary structure architecture. Generally, the tertiary structure comprises an eight stranded antiparallel beta-barrel and encloses an internal hydrophobic ligand binding domain. Additionally, the lipocalin family of proteins includes a $3_{10}$-like helix that is located on the inferior surface of the beta-barrel. The short $3_{10}$-helix, helps to close off one end of the barrel of the lipocalin protein thus allowing capture of a variety of hydrophobic molecules. The beta-barrel and $3_{10}$ helix are common to proteins within the larger lipocalin family.

Additionally, the structure of the lipocalin fold is dominated by eight beta-strands, which together form a calys- or cup-shaped antiparallel beta-barrel, which encloses an internal ligand binding site. (See, Flower et al., "Structure and sequence relationships in the Lipocalins and related proteins." Protein Science (1993), 2, 753-761)).

More specifically, the structure of the L1 includes a large omega-loop and generally forms a lid folded back to cap or close the internal ligand-binding site. The continuation of this loop varies in detail between different proteins of the lipocalin family but maintains its overall shape, size, and position. The L1 loop serves to close the internal ligand-binding site, which serves to enclose the ligand in the protein and prevent it from becoming detached from the protein. The $3_{10}$ alpha-helix then closes off the other end of the barrel. Accordingly, in conjunction these two particular components, the L1 loop and the $3_{10}$ alpha helix of the lipocalin protein encase the ligand.

Accordingly, in some embodiments herein, proteins having a similar beta-barrel structure, $3_{10}$ helix and/or L1 loop, may be utilized in the practice of the present disclosure. Moreover, proteins including a beta-barrel structure that are capable of binding hydrophobic ligands may be utilized in some embodiments in the practice of the present disclosure. As will be understood by one of ordinary skill in the art, proteins that include any molecular or structural modification of the beta-barrel, $3_{10}$ helix structure of the lipocalin family of proteins or the L1 loop at the opening of the ligand binding domain of the lipocalin family of proteins, may be utilized in the practice of the present disclosure. Further, in some embodiments, at least one lipocalin protein may include a genetically modified lipocalin protein. Potential genetic modifications include modification of the L1 loop or the $3_{10}$ alpha helixes at either end of the protein, as well as the internal structure of the protein itself. Moreover, in some embodiments, the at least one lipocalin protein may include a genetically modified lipocalin protein that has been modified so as to exhibit increased binding affinity of uremic toxins, and/or increase amount of protein binding (i.e. improved stoichiometry), both of which would improve the clearance of uremic toxins when utilized in practice of the present disclosure. In some embodiments, the at least one lipocalin protein may be a genetically modified lipocalin protein that is genetically modified by any process currently known in the art or later developed.

In some embodiments, the at least one lipocalin protein used in the dialysis apparatus of the present disclosure may be comprised of, but is not limited to, at least one or any combination of the following proteins: alpha-1-microglobulin (protein HC), major urinary proteins, alpha-1-acid glycoprotein (orosomucoid), aphrodisin, apolipoprotein D, beta-lactoglobulin, complement component C8 gamma chain, crustacyanin, epididymal-retinoic acid binding protein (E-RABP), insectacyanin, odorant binding protein (OBP), human pregnancy-associated endometrial alpha-2 globulin (PREP), probasin (PB), a prostatic protein, prostaglandin D synthase, purpurin, Von Ebner's gland protein (VEGP), and lizard epididymal secretory protein IV (LESP IV). In particular embodiments, the at least one or any combination of the following proteins includes: FABP1, FABP2, FABP3, FABP4, FABP5, FABP6, FABP7, LCN1, LCN2, LCN8, LCN09, LCN10, LCN12, OBP2A, OBP2B, RBP1, RBP2, RBP4, RBP5, RBP7, PAEP, PERF15, PMP2, PTGDS, AMBP, APOD, C8G, CRABP1, CRABP2, UNX2541, ORM1, and ORM2. The source at least one or any combination of proteins is not particularly limited. In some embodiments, the source of the proteins is mammalian, for example, such as canines, felines, bovines, caprines, equines, ovines, porcines, rodents (e.g. rats and mice), lagomorphs, primates (including non-human primates), etc. In one embodiment, the proteins are human proteins.

In other particular embodiments, the at least one or any combination of proteins includes: human lipocalin 1 (LCN1, for example, as set forth in GenBank/NCBI Accession Nos, NP_001239546.1, NP_002288.1, NP_001239547.1 and/or NP_001239548.1); human lipocalin 2 (LCN2, for example, as set forth in GenBank/NCBI Accession Nos. AAI-133089.1 and/or NP_—005555.2); human lipocalin 8 (LCN8, for example, as set forth in GenBank/NCBI Accession Nos. AAQ81973.1, NP_848564.2, XP_005266115.1, XP_006717016.1, AAI32715.1 and/or AAI30466.1); human lipocalin 9 (LCN9, for example, as set forth in GenBank/NCBI Accession Nos. AAQ81975.1, NP_001001676.1 and/or XP_006717169.1); human lipocalin 10 (LCN10, for example, as set forth in GenBank/NCBI Accession Nos. AAQ81976.1, AAI33046.1, and/or NP_001001712.2); human lipocalin 12 (LCN12, for example, as set forth in GenBank/NCBI Accession Nos. AAQ81977.1, NP_848631.2, XP_005266125.1_XP 005266126.1, XP_005266127.1, XP_005266128.1 and/or XP_005266129.1); human olfactory (odorant) binding protein isoform 2a (OBP2A, for example, as set forth in GenBank/NCBI Accession Nos. AAI-169563.1, NP_055397.1, NP_001280118.1, NP_001280122.1 and/or XP_006717150.1); human olfactory (odorant) binding protein isoform 2b (OBP2B, for example, as set forth in GenBank/NCBI Accession Nos, AAQ89340.1, AA1198340.1, NP_055396.1, NP_001275916.1 and/or XP_006717149.1); human retinol binding protein 1 (RBP1, for example, as set forth in GenBank/NCBI Accession Nos. NP_002890.2, NP_001124464.1 and/or NP_001124465.1); human retinol binding protein 2 (RBP2, for example, as set forth in GenBank/NCBI Accession Nos, NP_004155.2, XP_005247750.1 and/or XP_006713785.1); human retinol binding protein 4 (RBP4, for example, as set forth in GenBank/NCBI Accession Nos. NP_006735.2 and/or XP_005270080.1); human retinol binding protein 5 (RBP5, for example, as set forth in GenBank/NCBI Accession No. NP_113679.1); and/or human retinol binding protein 7 (RBP7, for example, as set forth in GenBank/NCBI Accession No. NP_443192.1).

OBPs are members of the lipocalin family of proteins and are found in the antennae of various insects. For the purposes of this disclosure, the terms "odorant binding protein" and "olfactory binding protein" may be used interchangeably relating to OBP. Human OBP2A (NCBI Accession No. NP_055397.1), for example, is comprised of 170 amino acids, however the first 15 amino acids code for a signal peptide that is cleaved off during protein synthesis. As such, the mature OBP2A peptide contains 155 amino acids. Generally, OBP2A is an eight-stranded, antiparallel, symmetrical β-barrel fold, which has been rolled into a cylindrical shape. Inside the barrel of the OBP2A protein is a ligand binding site. While specific information regarding post-translational modification of OBP2A is limited, there is a disulfide bridge formed between cysteines located at position 74 and 166 respectively. Further, serine 51 of rat OBP can be phosphorylated, but it is unknown whether this occurs in humans. See Jonathan Pevsner S, Vivian Hou, Adele M. Snowman, and Solomon H. Snyder. Odorant-binding Protein: Characterization and Ligand Binding J. Biol. Chem. Vol. 265, No. 11, Issue of April 15, pp. 6118-6125, 1990.

Accordingly, in some embodiments, the dialysis apparatus comprises at least one polysulfone membrane having at least one olfactory binding protein attached thereon. In some embodiments, the at least one olfactory binding protein may be selected from, but is not limited to the following: OBP2A, OBP2B and combinations thereof. In still some embodiments, the dialysis apparatus comprises at least one polysulfone membrane having a plurality of olfactory binding proteins bound thereon. In some embodiments, the dialysis apparatus comprises a disposable dialysis cartridge.

In some embodiments, the at least one lipocalin protein may be synthesized and purchased from a commercial company that specializes in the synthesis of complete proteins, for example, Bio-synthesis (Lewisville, Tex.). Further, in some embodiments, C-DNA vectors for one or more of the lipocalin protein(s) are expressed in yeast culture system. To minimize degradation of the expressed lipocalin proteins, generally all yeast cultures include a cocktail of various protease inhibitors. In some embodiments, confirmation that a specific lipocalin protein(s) has been expressed may be validated using SDS-PAGE electrophoresis and immunoblotting of western blots. In some embodiments, the lipocalin protein(s) are at least 70%; 75%, 80%, 85%, 90%, 95%, 99% or 100% free of contaminants. In some embodiments, the lipocalin protein(s) utilized in practice of the present disclosure will be at least 90% pure.

In some embodiments; at least one protein from the lipocalin family may be bound to the membrane by any method known in the art. For example; in some embodiments at least one lipocalin protein is bound to the membrane by a histidine tag, Any method known in the art for expressing a lipocalin protein with a histidine tag and/or multiple histidine residues may be utilized herein to attach the lipocalin protein to the membrane. In some embodiments, at least one lipocalin protein is covalently bonded to a polysulfone membrane by any method known in the art. In some embodiments, as a result of the nature of the synthesis of the lipocalin protein(s) by the commercial company, the lipocalin protein(s) will contain a histidine tag regardless of the cell type it is expressed in, that will be utilized in the binding of the protein to the cartridge membrane. In any instance, the binding is specific binding and not non-specific binding.

For example, in some embodiments, in order to bind the at least one protein from the lipocalin family, the vector encoding for a specific lipocalin protein will include a histidine tag. For example, in some embodiments, the carbolxylation reaction described, for example, in Möckel et al., *Journal of Membrane Science;* 158: 63-75, 1999; and Guiver et al., *British Polymer Journal;* 23: 29-39, 1990 are hereby incorporated by reference. Moreover, in some embodiments, the at least one lipocalin protein is bonded to the polysulfone membrane by exposing the at least one lipocalin protein including a histidine tag to a chelated polysulfone membrane in the presence of $Li^+$ or some other chelating metal such as $Ni^{2+}$ or $Co^{2+}$ in the presence of dry ice. This process will allow for the binding of histidine, which is located on the at least one lipocalin protein, to the chelated polysulfone membrane.

In some embodiments, the at least one protein from the lipocalin family may be bound (e.g., specific binding) to any suitable membrane known in the art. In some embodiments, the membrane selected may include but is not limited to any one or combinations of the following: polysulfone, polyethersulfone, AN69 (acrylonitrile membrane), and cellulose acetate. For example, in some embodiments the membranes used in the dialysis apparatus may include cellulose-based membranes, synthetic membranes and combinations therefor. Non-limiting examples of cellulose-based membranes include: cellulose acetate, triacetate, and combinations thereof. Non-limiting examples of synthetic membranes include: poly amide, polysulfone; polyethersulfone, polyacrylonitrile, polymethylmethacylate, and combinations thereof.

In some embodiments, the at least one membrane may be polyethersulfone. In some embodiments, the polyethersulfone membrane may be chemically modified to chelate a covalent ion to the membrane surface as described. See also Kroll et al., Journal of Membrane Science; 299: 181-189, 2007. In addition to polysulfone, in some embodiments the membrane selected may be a membrane having a similar structure to polysulfone.

Figure 1:
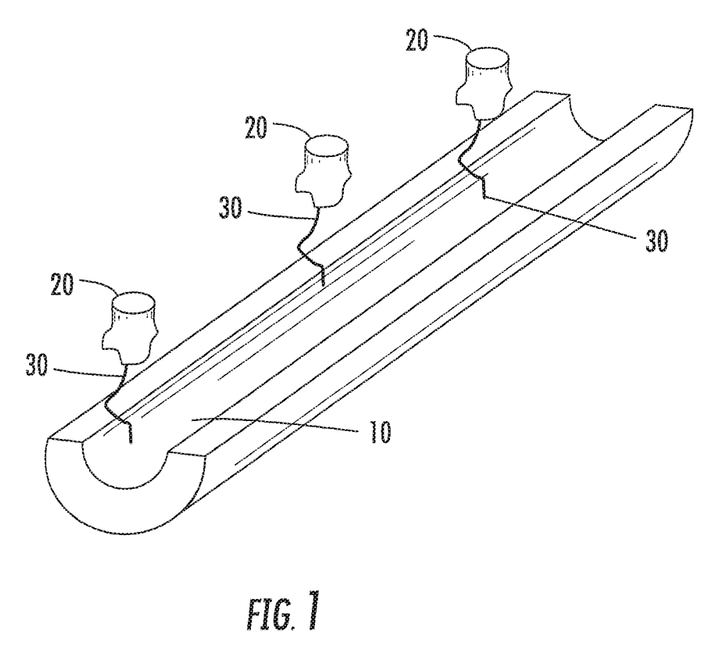
FIG. 1 is a schematic drawing of a polysulfone membrane having at least one lipocalin protein bound thereon.
Figure 2:
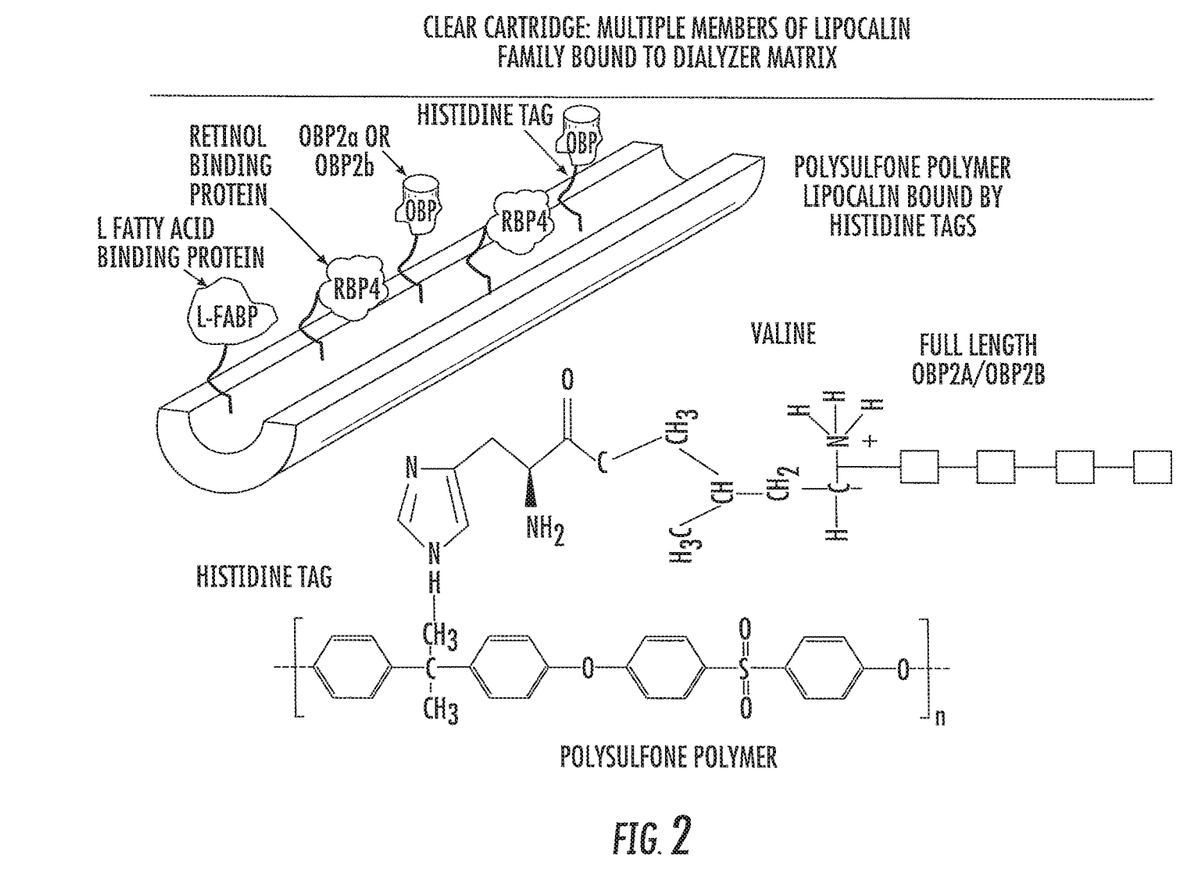
FIG. 2 is another schematic drawing of a polysulfone membrane having at east one lipocalin protein bound thereon.
Figure 3:
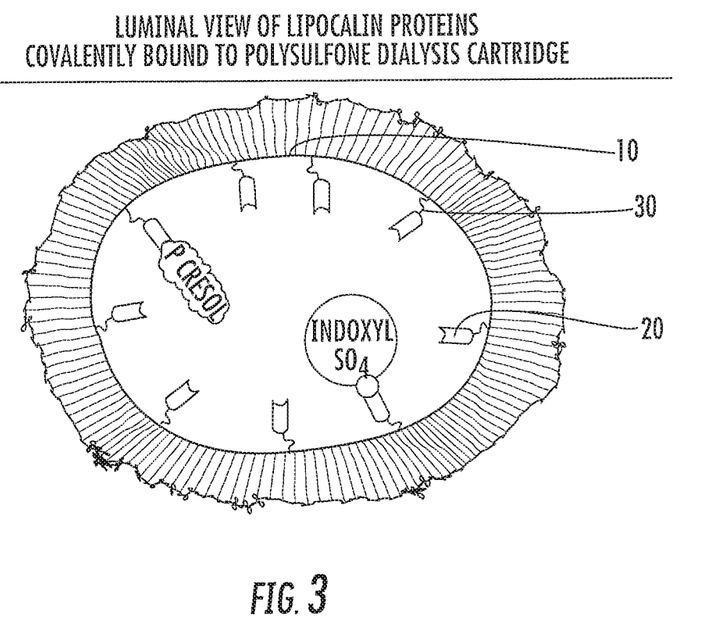
FIG. 3 is a schematic drawing of a Lumenal view of lipocalin proteins bound to a polysulfone membrane.

Briefly, FIG. 1 illustrates the interior of the body of the dialysis apparatus that includes at least one protein from the lipocalin family. As shown in FIG. 1, the polysulfone membrane 10 includes at least one protein from the lipocalin family 20 that is covalently bonded to the polysulfone membrane 10 via a histidine tag 30. Further, the polysulfone membrane, in some embodiments, includes a plurality of proteins from the lipocalin family 20. A further depiction of the interior of the body of a dialysis apparatus of the disclosure is shown in FIG. 2. FIG. 3 provides an illustration of the lumen of a polysulfone membrane having lipocalin proteins bound thereto.

Figure 4:
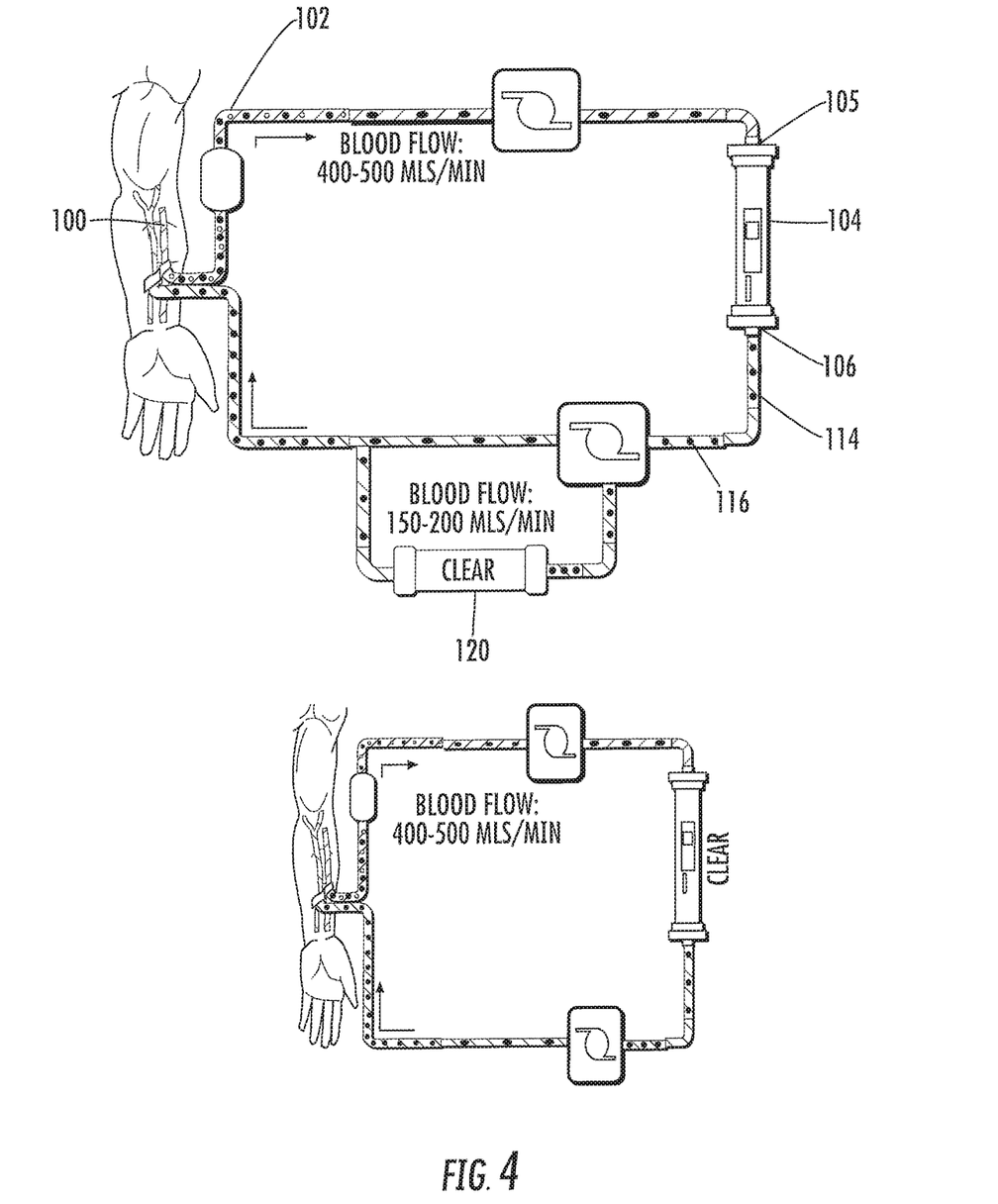
FIG. 4 illustrates schematically a system for performing dialysis using the dialysis apparatus described herein.

As shown in FIG. 4, a fluid waste stream 100 from a target subject enters a fluid flow path 102 and enters the dialysis apparatus 104. The dialysis apparatus 104 includes an inlet 105 and an outlet 106. As previously described in reference to FIG. 1, the interior of the dialysis apparatus includes at least one protein from the lipocalin family (not shown in FIG. 4). In some embodiments, the dialysis apparatus 104 is a dialysis cartridge. The fluid waste stream 100 may or may not have been treated prior to entering the dialysis apparatus 104. As the fluid waste stream passes through the dialysis apparatus 104, the non-polar, hydrophobic, or protein bound uremic toxins are removed from the fluid waste stream 100 as they come into contact with the protein(s) from the lipocalin family that is bound to the interior of the dialysis apparatus 104. As a result of passing through the dialysis apparatus 104, a clean fluid stream 114, void of or having a lower concentration of non-polar, hydrophobic, or protein bound uremic, toxins emerges from the outlet 106 of the dialysis apparatus 104. The clean fluid stream 114 may have up to 70%, 75%, 80%, 85%, 90%, 95%, 99% or 100% lower concentration of non-polar, hydrophobic, or protein bound uremic toxins. The final clean fluid stream 114 then exits the dialysis apparatus 104 via the outlet 106 and enters a fluid flow path 116 and then goes back to the target subject.

In some embodiments, the dialysis apparatus 104 may comprise additional filters, for example, in some embodiments, the dialysis apparatus 104 may include a filtration membrane that is capable of retaining charged species such as Ca2+, Mg2+, Na+ and proteins.

In certain embodiments, to improve the treatment capacity of the dialysis apparatus 104, the flow rate of the fluid waste stream 100 should be sufficiently long enough to allow the non-polar, hydrophobic, or protein bound uremic toxins to bind with the proteins from the lipocalin family located within the dialysis apparatus 104. For example, in some embodiments the flow rate of the fluid waste stream 100 may be from about 200 mls/min to about 600 mls/min. In still some embodiments, the flow rate of the fluid waste stream 100 may be from about 300 mls/min to about 500 mls/min. Still in other embodiments, the fluid waste stream 100 may be from about 350 mls/min to about 450 mls/min.

In some embodiments, the flow rate of the clean fluid stream 114 after leaving the dialysis apparatus 104 and returning to the target subject is from about 50 mls/min to about 300 mls/min. In still some other embodiments, the flow rate of the clean fluid stream 114 is from about 100 mls/min to about 200 mls/min.

Additionally, in some embodiments, ions and/or fluids can be replaced in the stream, for example, through the addition of concentrated dialysis components such as osmotic agents (e.g., dextrose, icodextrin, glucose polymers, glucose polymer derivatives, amino acids), buffers (e.g., lactate, bicarbonate) and electrolytes (e.g., sodium, potassium, calcium, magnesium) from a suitable fluid source.

In some embodiments, a pump may be used to propel the fluid waste stream into the fluid flow path 102, through the dialysis apparatus 104, into a second fluid flow path 116 and back to the target subject. Any pump known or used in the art may be utilized herein. In some embodiments a first pump may be used to pump the fluid waste stream 104 from the target subject into the dialysis apparatus 104, while a second pump may be utilized to pump the clean fluid stream from the dialysis apparatus 104 back to the target subject. In still other embodiments, at least one flow restrictor and/or at least one pump may be used to create pressure gradients. In this regard, the at least one flow restrictor and/or at least one pump can provide a sufficiently high pressure to force fluid through the dialysis apparatus 104 and fluid flow paths 102 and 114.

In some embodiments, the clean fluid stream 114 may be passed through a clear cartridge 120 before re-entering the target subject. As shown in FIG. 4, in some embodiments, the clean fluid stream 114 may bypass the clear cartridge 120 and re-enter the target subject, and in other embodiments, the clean fluid stream 114 enters a separate fluid flow path 112 which allows the clean fluid stream 114 to pass through the clear cartridge 120 before re-entering the target subject.

Additionally, disclosed herein are methods of removing non-polar, hydrophobic, and/or protein bound toxins from a target subject comprising utilizing a dialysis apparatus wherein the dialysis apparatus comprises at least one membrane having at least one protein selected from the lipocalin family bound thereon. In some embodiments, the at least one membrane is a polysulfone membrane. In some embodiments, the methods disclosed herein may comprise the steps of inserting a catheter or other suitable device into the target subject to remove blood from the target subject, passing or transferring the blood through a fluid flow path and into the dialysis apparatus disclosed herein. Moreover, in some embodiments, additional filtration or dialysis techniques known in the art may be utilized prior to passing the blood from the target subject into the dialysis apparatus disclosed herein. In still some embodiments, methods of removing non-polar, hydrophobic and/or protein bound uremic toxins from a target subject comprising using a dialysis apparatus may further comprise using a priming solution that is passed through the cartridge prior to use. The solution includes one or more lipocalins that would attach to the dialysis cartridge membrane as described with respect to the self-contained cartridge including the lipocalins and other components as described above.

In some embodiments the methods disclosed herein may further comprise the step of passing the blood through the dialysis apparatus such that the blood comes into contact with the at least one protein from the lipocalin family, which is bound to the blood side of the membrane. In some embodiments, the membrane is a polysulfone membrane. Still in some embodiments, the method(s) may further comprise the step of passing the blood through the dialysis apparatus such that the blood comes into contact with at least one OBP. In some embodiments, the OBP may be bound to a polysulfone membrane.

In some embodiments, the blood is passed through the polysulfone membrane at an effective flow rate. The effective flow rate is, generally, the rate that allows for non-polar, hydrophobic, and/or protein bound uremic toxins to bind to the at least one protein from the lipocalin family. The optimal flow rate to maximize the binding of non-polar toxins to the lipocalin proteins can be determined by one of ordinary skill in the art without undue experimentation. In embodiments where the polysulfone membrane comprises a plurality of proteins from the lipocalin family, the plurality of proteins removes the non-polar, hydrophobic, and/or protein bound toxins, thereby effectively reducing the amount of or eliminating these toxins from the blood.

In some embodiments, the at least one lipocalin protein is selected from OBP2A, OBP2B, and combinations thereof in still other embodiments, the at least one polysulfone membrane may comprise a plurality of OBP2A bound thereon. In still other embodiments, the at least one polysulfone membrane may comprise a plurality of OBP2B bound thereon. In still some embodiments, the at least one polysulfone membrane may comprise a plurality of OBP2A and OBP2B bound thereon.

In some embodiments, the dialysis apparatus or cartridge of the present invention is modified internally such that the flow of blood creates "edifies" and areas where the interface between the circulating blood and the attached lipocalins is maximized. In still other embodiments, these dams and structural modifications are designed to maximize binding for specific combinations of lipocalins. In still other embodiments, the dialysis apparatus or cartridge of the present invention with specific combinations of lipocalins, dams and blood flow specifications are designed to meet the metabolic needs of individual patients. Additionally, the methods disclosed herein may further include the steps of removing the cleaned blood from the dialysis apparatus disclosed herein, passing the cleaned blood through a fluid flow path, and/or returning the cleaned blood to the target subject. The cleaned blood may be returned to the target subject via any suitable method known in the art, such as via a catheter. Additional filtration and/or dialysate techniques as known in the art may be further administered prior to passing the cleaned blood back to the target subject.

Non-limiting examples of non-polar, hydrophobic, and/or protein bound uremic toxins that may be removed via the dialysis apparatus and methods disclosed herein include: p-cresol, p-cresyl sulfate, indoxyl sulfate. 3-carboxy-4-methyl-5-propyl-2-furanpropanoic acid, hippuric acid, indoleacetic acid, and combinations thereof. Moreover, Vanholder et al., "Review on uremic toxins: Classification, concentration, and interindividual variability" *Kidney International*, Vol. 63, (2003), pp. 1934-1943, which is incorporated by reference in its entirety herein, discloses uremic toxins which may be removed via the dialysis apparatus and/or methods disclosed herein. (See Vanholder et al., Table 1, Table 2, and Table 3).

The non-polar uremic toxins removed by the dialysis apparatus or methods disclosed herein may exist as free substances or may bind to serum proteins, such as albwnin. Accordingly, in some embodiments, the dialysis apparatus and methods disclosed herein are directed to removing at least one non-polar uremic toxin that is bound to a serum protein. For example, in some embodiments, this includes the removal of at least one non-polar uremic toxin that is bound to albumin.

Further, disclosed herein is a method of removing at least one non-polar uremic toxin from the blood of a target subject comprising the steps of passing the blood of a target subject through a dialysis apparatus, wherein the dialysis apparatus comprises at least one polysulfone membrane having at least one protein from the lipocalin family bound thereon, wherein the non-polar uremic toxin binds to the at least one protein form the lipocalin family and is removed from the blood of a target patient. In some embodiments, the non-polar uremic toxin that is removed is p-cresol. In still some embodiments, the at least one non-polar uremic toxin is a free substance. In still some embodiments, the at least one non-polar uremic toxin is bound to at least one serum protein.

The present disclosure further provides methods of preventing or treating uremia including uremic clinical symptoms and side effects. Uremic clinical symptoms and side effects include, but are not limited to, fatigue, anemia, itching, peripheral neuropathy, gastrointestinal disorders including nausea, vomiting, diarrhea, cardiovascular complications including accelerated coronary and peripheral vascular disease, left ventricular hypertrophy, cardiac fibrosis and accelerated rates of arrhythmias. In some instances, the uremia arises from hydrophobic, protein-bound uremic toxins.

Additionally, the present disclosure provides methods of utilizing one or more lipocalin proteins described herein bound (e.g., specific binding) in an apparatus of the present invention as described herein for the purpose of removing prescription and/or non-prescription drugs from a bodily fluid of a subject. In some embodiments, the presence prescription or non-prescription drugs in the subject's bodily fluid results from an accidental or intentional overdose. In some embodiments, the drug includes, but is not limited to, acetaminophen, phenytoin (Dilantin), lorazepam (Ativan), warfarin (Coumadin), tricyclic antidepressants, digoxin, theophylline, valproic acid, carbamazepine (Tegretol), and cocaine.

"Subject" as used herein is a subject in whom renal dialysis is needed or desired. A subject may be a patient. In some embodiments, the subject is a human; however, a subject of this disclosure can include an animal subject, particularly mammalian subjects such as canines, felines, bovines, caprines, equines, ovines, porcines, rodents (e.g. rats and mice), lagomorphs, primates (including non-human primates), etc., including domesticated animals, companion animals and wild animals for veterinary medicine, treatment or pharmaceutical drug development purposes.

The subjects relevant to this disclosure may be male or female and may be any species and of any race or ethnicity, including, but not limited to, Caucasian, African-American, African, Asian, Hispanic, Indian, etc., and combined backgrounds. The subjects may be of any age, including newborn, neonate, infant, child, adolescent, adult, and geriatric.

In some embodiments, the subject has impaired kidney function, kidney disease, acute kidney disease, chronic kidney disease, advanced kidney disease or end stage renal disease (ESRD). In some embodiments, the subject can have any type of primary disease that leads to impaired glomerular filtration rate (GFR) including, but not limited to diabetes, hypertension or glomerulonephritis.

In some embodiments, the subject is one in whom prescription or non-prescription drug clearance or removal is needed or desired. Further, the subject can be a patient in a medical facility, hospital setting, ambulatory care setting, urgent or critical care setting, emergency medical services setting, drug rehabilitation setting, and the like. In some embodiments, the subject may be suffering from acute or chronic prescription or non-prescription drug toxicity. In some embodiments, the subject has experienced an accidental or intentional prescription or non-prescription drug overdose. In some embodiments, the subject is one in whom medical management of prescription or non-prescription drug overdose is desired.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Having now described the invention, the same will be illustrated with reference to certain examples, which are included herein for illustration purposes only, and which are not intended to be limiting of the invention.

EXAMPLES

Prophetic Experiments Confirming Efficacy of Lipocalin Modified Dialysis Cartridges Experiment 1: Initial experiments will establish the concentrations of P-cresol and where the fluorescence is linear and use this concentration range for the following prophetic experiments. Our initial experiments will be determine the binding affinity, dissociation constants (Kd) and molar stoichiometry of olfactory binding protein OBP-2a and OBP-2b and retinal binding protein-RBP-4 and other lipocalin molecules to free p-cresol, indoxyl sulfate, and other non-polar protein bound uremic toxins. The following table lists, but is not limited to uremic and protein bound toxins that will be studied.

TABLE 1

Uremic and protein bound toxins

| Solute | Group | $C_N$ | $C_U$ | $C_{Max}$ |
|---|---|---|---|---|
| 2-methoxy-resorcinol | phenols | — | 19.6 ± 81.2 | 322.0 |
| 3-deoxyglucosone | AGE | 0.3 ± 0.1 | 1.7 ± 1.0 | 3.5 |
| CMPF | | 7.7 ± 3.3 | 61.0 ± 16.5 | 94.0 |
| fructoselysine | AGE | — | 58.1 ± 10.8 | 79.7 |
| glyoxal | AGE | 67.0 ± 20.0 | 221.0 ± 28.0 | 277.0 |
| hippuric acid | hippurates | <5.0 | 247.0 ± 112.0 | 471.0 |
| hydroquinone | phenols | <1.7 | 8.1 ± 1.6 | 26.4 |
| indole-3-acetic acid | indoles | — | 50.6 ± 84.7 | 286.0 |
| indoxyl sulfate | indoles | 17.5 ± 17.5 | 875.0 ± 560.0 | 9076.9 |
| kinurenine | indoles | 0.6 ± 5.4 | 53.0 ± 91.5 | 236.0 |
| kynurenine | indoles | <391 | 686.4 ± 178.9 | 952.6 |
| kynurenic acid | indoles | <1.0 | — | 9.5 |
| leptin | peptides | 8.4 ± 6.7 | 72.0 ± 60.6 | 490.0 |
| melatonin | indoles | 26.5 ± 7.1 | 175.8 ± 130.2 | 436.2 |
| methylglyoxal | AGE | 47.0 ± 12.0 | 110.0 ± 18.0 | 146.0 |
| $N^\epsilon$-(carboxymethyl)lysine | AGE | 1.1 ± 0.3 | 4.3 ± 1.3 | 6.9 |
| p-cresol | phenols | 0.6 ± 1.0 | 20.1 ± 10.3 | 40.7 |
| pentosidine | AGE | 51.6 ± 18.8 | 896.0 ± 448.0 | 2964.0 |
| phenol | phenols | 0.6 ± 0.2 | 2.7 ± 3.9 | 10.5 |
| P-OHhippuric acid | hippurates | — | 18.3 ± 6.6 | 31.5 |
| putrescine | polyamines | 21.1 ± 7.9 | 77.4 ± 27.3 | 132.0 |
| quinolinic acid | indoles | 0.1 ± 0.05 | 1.5 ± 0.9 | 3.3 |
| retinol-binding protein | peptides | <80 | 192.0 ± 78.0 | 369.2 |
| spermidine | polyamines | — | 97.2 ± 45.0 | 187.2 |
| spermine | polyamines | — | 18.2 ± 16.2 | 66.7 |

CMPF = 3-carboxy-4methyl-5-propyl-2-furanpropionic acid
AGE = advanced glycation end products
$C_N$ = normal concentration (means ± SD or maximum value)
$C_U$ = mean/median uremic concentration (means ± SD or maximum value)
$C_{max}$ = maximal uremic concentration Example 1

Using agarose beads bound with C-Myc antibodies, the capacity of OBPs and RBPs and all other lipocalins to displace p-cresol, p-cresol sulfate and all other polar and non-polar protein bound uremic toxins from albumin binding stores will be established. Studies to confirm this observation will be performed as follows.

In brief, agarose beads bound with anti-C-Myc antibodies will be incubated with C-myc labeled OBP2a, OBP2b and RBP-4. One ml of labeled agarose beads will to bind 7.0 nMoles of C-myc tagged lipocalins.

The C-Myc antibody tagged agarose beads will be loaded into Sigma SC-100-Sigma. Prep Spin affinity columns and then washed with 400 ul phosphate buffered saline pH-7.4 containing 15 mM Na+ azide as preservative.

Sigma spin columns will be centrifuged at approximately 8200× g (10,000 rpm in an Eppendorf 54150 microcentrifuge) for 1" to remove wash buffer followed by the addition of 3.0 nMoles of C-Myc tagged OBP2a, OBP2b or RBP-4. Columns will be incubated at room 25oc for 1 hour.

OBP-lipocalin labeled affinity columns will be incubated with increasing concentration of p-cresol, p-cresol sulfate and indoxyl sulfate to confirm the binding affinity of the lipocalins for the non-polar, protein bound uremic toxins.

After thorough washing of the column of the eluents will be combined and the final concentration of p-cresol determined by Ultra-High Pressure Liquid Chromatography (U-HPLC). HPLC methods are outlined in brief.

Ultra-High Pressure Liquid Chromatography will be performed as outlined in Pretorius, C. J., McWhinney, B. C., Bilyana Sipinkoski, B., Johnson, L. A., Megan Rossi, M., Campbell, K., Ungerer, P. J. J. Reference ranges and biological variation of free and total serum 2 indoxyl- and p-cresol sulphate measured with a rapid UPLC 3 fluorescence detection method. Clin Chim Acta. 18; 419:122-6. 2013. Chemicals will be purchased from Sigma (USA):3-indoxyl-sulphate potassium salt (IS), p-cresol, 4-ethylphenol, pyrimidine, diethyl ether and sodium-octanoate. Acetonitrile, ethanol, methanol and water were HPLC grade. Chromatography will be performed with a Waters Acquity UPLC I class system comprising of a binary solvent manager, flow through needle autosampler, fluorescence detector and column manager (Milford Mass., USA) and an Acquit), HSS T3 1.8 µm (2.1×50 mm) column with an Acquity BEH C18 1.7 µm VanGuard pre-column (2.1×5 mm). Mobile phase A will be 50 mmol/L ammonium formate (pH 5.0) and mobile phase B was 100% acetonitrile. Mobile phase B increased with a linear gradient from 5 to 25% over 2.1 min, and will be maintained isocratically at 70% for 0.4 min, followed by 0.5 min at 99%. The column will be re-equilibrated with initial conditions for 0.5 min. The load-ahead facility within the system will be enabled to minimize the run time. Injection volume will be 2 µL for total IS (tIS) and total pCS (tpCS) and 5 µL for 95 fIS and fpCS samples. Column temperature was maintained at 45° C. IS eluted at 1.5 min, pCS at 2.1 min and the internal standard at 2.65 min. IS, pCS and the internal standard (50 µmol/L) 4-ethylphenol) will be quantified with timed programmed fluorescence detection monitoring at specific excitation/emission wavelengths (IS: 300/390 nm; pCS: 260/283 nm; and 4-ethylphenol: 285/310 nm). Calibrators, quality control and sample preparation calibrators, for tpCS and tIS will be prepared in saline spanning a range of 1 to 500 µmol/L, and for fpCS and fIS of 0.1 to 100 µmol/L. Quality control samples will be prepared by spiking pooled serum to obtain three levels as described in Table 1. Aliquots of the quality control materials will be stored at −80° C. fpCS and fIS measured directly, without addition of an internal standard, on ultrafiltrates prepared at room temperature from 200 µL of serum centrifuged for 10 min at 13,000 rpm with a 30,000 MWCO filter (Merck, Kilsyth, Australia). tIS and tpCS will be measured after deproteinization of 100 µL or albumin or serum solutions using 300 µL of ethanol containing internal standard (50 µmol/L 4-ethylphenol). The mixture will be centrifuged for 5 min at 13,000 rpm and poured into a 2.0 mL tube that contained 200 µL H$_2$O and 1 mL dichloromethane. After vortexing for 1 min and centrifuging for 5 min at 13,000 rpm, 150 µL of the aqueous supernatant was transferred to an injection vial. To compare ethanol vs. protein displacement, 100 µL of serum was added to 100 µL of 0.25 M sodium octanoate (binding competitor). After incubation at room temperature for 10 min, 600 µL ethanol with internal standard will be added prior to extraction into dichloromethane.

Example 2

The above experiments will be extended to establish the ability of OBP2a, OBP2b and RBP-4 and other lipocalins to remove p-cresol and other protein bound uremic toxins from albumin and other proteins in human serum. Increasing concentrations of p-cresol will be incubated with a physiologic concentration of human albumin (4.0 gm/dl) and then subjected to affinity chromatography as outlined in steps 1-4. The column eluents, which will contain a mixture of free and bound p-cresol, will be separated using U-HPLC and the concentration of p-cresol that did not bind to the lipocalin column determined. These experiments will be repeated using human serum and human albumin.

Example 3

Tertiary experiments will extend the observations of Steps 1-5 and examine the role of pH on the binding affinity of OBPs and other lipocalins for p-cresol and indoxyl sulfate. The rationale is that the high pH of bicarbonate dialysate could potentially alter the binding affinity of dialyzer bound lipocalins for p-cresol and other protein bound uremic toxins. These experiments will determine whether lipocalin modification of existing polysulfone dialyzers could lead to the creation of a single dialysis cartridge capable of simultaneously clearing both water soluble and water-insoluble uremic toxins.

Methods: These experiments will be conducted in a manner similar to Experiment 1 and 2. In brief, the role of changing pH on the level of p-cresol fluorescence that arises from binding to lipocalin proteins will be examined. These experiments will be extended to include normal and human serum from patients with pre-dialysis CKD and stable ESRD patients. In each of these latter experiments, the pH will be raised from 6.0 to 8.0 and the level of fluorescence measured.

Example 5

These studies will calculate the optimal flow rates for removal of p-cresol and other protein bound uremic toxins by OBPs and other lipocalins. Binding capacities will be calculated from 50-500 mls/min.

Methods: In brief, histamine tagged lipocalins will be bound to nickel coated columns. Varying concentrations of p-cresol in saline, albumin solutions or human serum will run through the column at increasing flow rates: ranging from 5.0 ml/min up to a maximum of 500 mls/min. The p-cresol bound OBPs will then be released from the column and the degree of fluorescence measured as previously recorded.

Example 6

Using a porcine model of chronic kidney disease (Collaboration with Medical College of Georgia) to determine whether bulk removal of non-polar protein bound uremic toxins will block the degradation of Connexin 43; a protein implicated in gap junction propagation of excitation potential across cardiac myocytes. The studies in Example 6 will create a porcine model of chronic renal failure using unilateral nephrectomy and ⅔ contralateral nephrectomy. CKD pigs will be sacrificed at 3 months and the level of plasma p-cresol quantified by U-HPLC as discussed previously correlated with the level of Connexin-43 expression in cardiac myocytes. The rationale is that cell culture models have shown that at concentrations commonly found among ESRD patients, p-cresol can induce a dose-dependent degradation of Connexin-43 within cardiac gap junctions. Connexins, or gap junction proteins, are a family of structurally related transmembrane proteins that assemble to form gap junctions, Each gap junction is composed of two hemichannels, or connexons, which is composed of six connexin molecules. Connexins in one cell connect with connexins in adjacent cells across the gap junction, connecting the cells electrically. Atrial fibrillation (AF) can be associated with a change in the number of connexins between cells. AF can also be associated with a change in connexin distribution, particularly lateralization of connexins. See Peng, Y. S., Ding, H. S., Lin, Y. T., Syu, J. P., Chen, Y., Wang, S. M. Uremic toxin p-cresol induces disassembly of gap junctions of cardiomyocytes Toxicology 302 (2012) 11-17.

These experiments will be extended by studying four animal groups: Group-1 normal controls, Group-2 CKD pigs without intervention, Group-3 CKD pigs treated with daily plasma phoresis for 1 week and Group-4 CKD pigs treated with daily plastnaphoresis and receiving daily infusion of p-cresol. Because p-cresol rapidly degrades Connexin-43 and the loss of this protein contributes to atrial arrhythmias, it is believed that Group-3 subjects will exhibit Connexin-43 levels that approximate those of the normal controls.

Example 7

These studies will build an experimental parallel plate dialyzer prototype of the CLEAR cartridge where the process of covalently binding proteins from the lipocalin family to sheets of polysulfone material will be refined. The plate dialyzer technology will be applied to the CKD pig models where the biologic endpoint of p-cresol removal will be restoration of Connexin-43 expression in cardiac gap junctions. These experiments will be extended to creation of a CLEAR cartridge using polysulfone hollow fiber dialysis membranes.

Example 8

These studies will extend the findings of Example 7 and a Phase trial to determine the safety and efficacy of the CLEAR cartridge in patients with ESRD will be conducted.

Example 9

These studies will include a randomized prospective trial comparing conventional hemodialysis with hemodialysis and the CLEAR cartridge technology in the following clinical complications of End Stage Renal Disease (ESRD).

Rate of post dialysis bradycardia and incidence of Atrial or Ventricular arrhythmia.

Determining the rate of development of Left ventricular hypertrophy (LVH) and diastolic dysfunction in incident dialysis patients Determine the efficacy of the CLEAR cartridge technology on the incidence and severity of uremic Pruritis Determine the efficacy of the CLEAR cartridge technology on cognition, rates of depression and other neuropsychiatric complications of ESRD Determine the efficacy of the CLEAR cartridge technology on olfactory capabilities in ESRD patients Determine the efficacy of the CLEAR cartridge technology in reducing the rate of malaria infection in ESRD that are in countries with endemic populations of malaria.

Prophetic Experiments Confirming Efficacy of Lipocalin Modified Dialysis Cartridges Binding and Clearance of Protein Bound Poisons and Drug Overdoses Example 1

To expand the utility of a lipocalin modified dialysis cartridge, we will perform preliminary experiments documenting the ability of lipocalins as described herein, and in particular, OBP2a, OBP2b, RBP4, and LFABP, to bind and remove highly protein bound drugs from the plasma. The principal clinical application of this extension is the use of the CLEAR cartridge to remove potentially life threatening drug overdoses. Drugs that will be tested for lipocalin binding and drug removal include, but are not limited to the following drugs, acetaminophen, phenytoin (Di lantin), lorazepam (Ativan), warfarin (Coumadin), tricyclic antidepressants, digoxin, theophylline, valproic acid, carbamazepine (Tegretol), and cocaine.

The molar to molar binding affinity of the above drugs that have been consistently reported to be a cause of drug overdose will be investigated for their ability to bind and be cleared by lipocalins bound to a membrane as described herein. The same methods used in the experiments described above will be used to confirm the binding of drugs to the CLEAR cartridge at flow rates compatible for conventional dialysis machines.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. Therefore, the spirit and scope of the appended claims should not be limited to the description of the versions contained therein.

What is claimed is:

1. A method of dialysis to remove a nonpolar, hydrophobic, and/or protein-bound uremic toxin from the blood or plasma of a subject, comprising subjecting the blood or plasma to an apparatus comprising a body having an inlet and an outlet and defining an interior, the interior including a membrane having a lipocalin family protein covalently bound thereon, the lipocalin family protein being one that binds to the uremic toxin, the apparatus being arranged so that the blood or plasma entering the apparatus contacts the lipocalin family protein in the interior of the apparatus.

2. The method of claim 1, where the lipocalin family protein is selected from the group consisting of alpha-1-microglobulin (protein HC), major urinary proteins, alpha-1-acid glycoprotein (orosomucoid), aphrodisin, apolipoprotein D, beta-lactoglobulin, complement component C8 gamma chain, crustacyanin, epididymal-retinoic acid binding protein (E-RABP), insectacyanin, odorant binding protein (OBP), human pregnancy-associated endometrial alpha-2 globulin (PAEP), probasin (PB), prostatic proteins, prostaglandin D synthase, purpurin, Von Ebner's gland protein (VEGP), lizard epididymal secretory protein IV (LESP IV), and combinations thereof.

3. The method of claim 1, where the lipocalin family protein is selected from the group consisting of FABP1, FABP2, FABP3, FABP4, FABP5, FABP6, FABP7, LCN1, LCN2, LCN8, LCN09, LCN10, LCN12, OBP2A, OBP2B, RBP1, RBP2, RBP4, RBP5, RBP7, PAEP, PERF15, PMP2, PTGDS, AMBP, APOD, C8G, CRABP1, CRABP2, UNX2541, ORM1, and ORM2, and combinations thereof.

4. The method of claim 1, where the lipocalin family protein comprises a plurality of proteins of the same type.

5. The method of claim 1, where the lipocalin family protein comprises a plurality of proteins of different types.

6. The method of claim 1, where the lipocalin family protein is an odorant binding protein.

7. The method of claim 1, where the membrane comprises polyamide, polysulfone, polyethersulfone, cellulose acetate, triacetate, polyacrylonitrile, or polymethylmethacrylate.

8. The method of claim 1, where the uremic toxin comprises p-cresol, indoxyl sulfate, or p-cresol sulfate.

\* \* \* \* \*